United States Patent
Kozono et al.

(10) Patent No.: US 7,737,296 B2
(45) Date of Patent: Jun. 15, 2010

(54) METHOD FOR PRODUCING 2-HYDROXYESTER COMPOUND

(75) Inventors: Ichiro Kozono, Mobara (JP); Naoki Fujiwara, Chiba (JP); Daisuke Hino, Mobara (JP)

(73) Assignee: Nippoh Chemicals Co., Ltd., Chuo-Ku, Tokyo (JP)

( * ) Notice: Subject to any disclaimer, the term of this patent is extended or adjusted under 35 U.S.C. 154(b) by 0 days.

(21) Appl. No.: 11/997,856

(22) PCT Filed: Aug. 8, 2006

(86) PCT No.: PCT/JP2006/315686

§ 371 (c)(1),
(2), (4) Date: Mar. 12, 2008

(87) PCT Pub. No.: WO2007/018221

PCT Pub. Date: Feb. 15, 2007

(65) Prior Publication Data

US 2008/0214861 A1 Sep. 4, 2008

(30) Foreign Application Priority Data

Aug. 8, 2005 (JP) .............................. 2005-229970

(51) Int. Cl.
*C07C 69/66* (2006.01)
(52) U.S. Cl. .................................................... 560/179
(58) Field of Classification Search .................. None
See application file for complete search history.

(56) References Cited

U.S. PATENT DOCUMENTS 2,041,820 A 5/1936 Crawford (Continued)

FOREIGN PATENT DOCUMENTS

EP 0 463 676 (A1) 1/1992

(Continued)

OTHER PUBLICATIONS

Fosdick et al., Journal of the American Chemical Society (1938), 60, 1465-6.*

(Continued)

*Primary Examiner*—Karl J Puttlitz
(74) *Attorney, Agent, or Firm*—Buchanan Ingersoll & Rooney PC

(57) ABSTRACT

A simple and easy-to-use method for producing a 2-hydroxyester compound using a cyanohydrin compound, as a raw material, is provided. A method for producing a 2-hydroxyester compound represented by the general formula (1) (provided that ethyl 2-hydroxy-4-phenylbutyrate is excluded), wherein an acid is introduced into a mixture of a cyanohydrin compound represented by the general formula (2), an alcohol, an organic solvent and water:

(Chemical Formula 1)

$$R^1-CH(OH)-COOR^2 \quad (1)$$

$$R^1-CH(OH)(CN) \quad (2)$$

wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

24 Claims, 1 Drawing Sheet

U.S. PATENT DOCUMENTS

| | | | |
|---|---|---|---|
| 5,175,345 | A | 12/1992 | Terada et al. |
| 7,094,920 | B2 | 8/2006 | Tikare |

FOREIGN PATENT DOCUMENTS

| | | | |
|---|---|---|---|
| EP | 463676 | * | 1/1992 |
| JP | 4-230241 (A) | | 8/1992 |
| JP | 5-058953 (A) | | 3/1993 |
| JP | 6-247895 (A) | | 9/1994 |
| JP | 6-247896 (A) | | 9/1994 |
| JP | 6247896 | * | 9/1994 |
| JP | 2004-534040 (T) | | 11/2004 |
| JP | 2004-346022 (A) | | 12/2004 |
| JP | 2006-219421 (A) | | 8/2006 |
| WO | WO 2004/092114 A1 | | 10/2004 |

OTHER PUBLICATIONS

Abstract, CAS online citation 32:41776 [retrieved Oct. 20, 2008] from STN; Columbus, OH, USA.*

Form PCT/ISA/210 (International Search Report) dated Sep. 19, 2006.

Non-English language version of Form PCT/ISA/237 (Written Opinion of the International Searching Authority) dated Sep. 6, 2006.

Form PCT/ISA/237 (Written Opinion of the International Searching Authority).

A Search Report issued Nov. 16, 2009 in corresponding European Application No. 06782512.

Makoto Takamura et al., "Efficient Synthesis of Antihyperglycemic (S)-α-Aryloxy-β-phenylpropionic Acid Using a Bifunctional Asymmetric Catalyst," Chemical & Pharmaceutical Bulletin, vol. 50, No. 8, Aug. 1, 2002, pp. 1118-1121, XP002551764.

Jose L. Garcia Ruano et al., "A New General Method to Obtain Chiral 2-Alkylglycidic Acid Derivatives: Synthesis of Methyl (R)-(+)-Palmoxirate," The Journal of Organic Chemistry, vol. 59, No. 3, Feb. 1994, pp. 533-536, XP002551763.

Yvonne Lear et al., "Synthesis of Regiospecifically Substituted 2-Hydroxybenzocyclobutenones," Canadian Journal of Chemistry, vol. 75, No. 6, Jun. 1997, pp. 817-824, XP002551765.

* cited by examiner

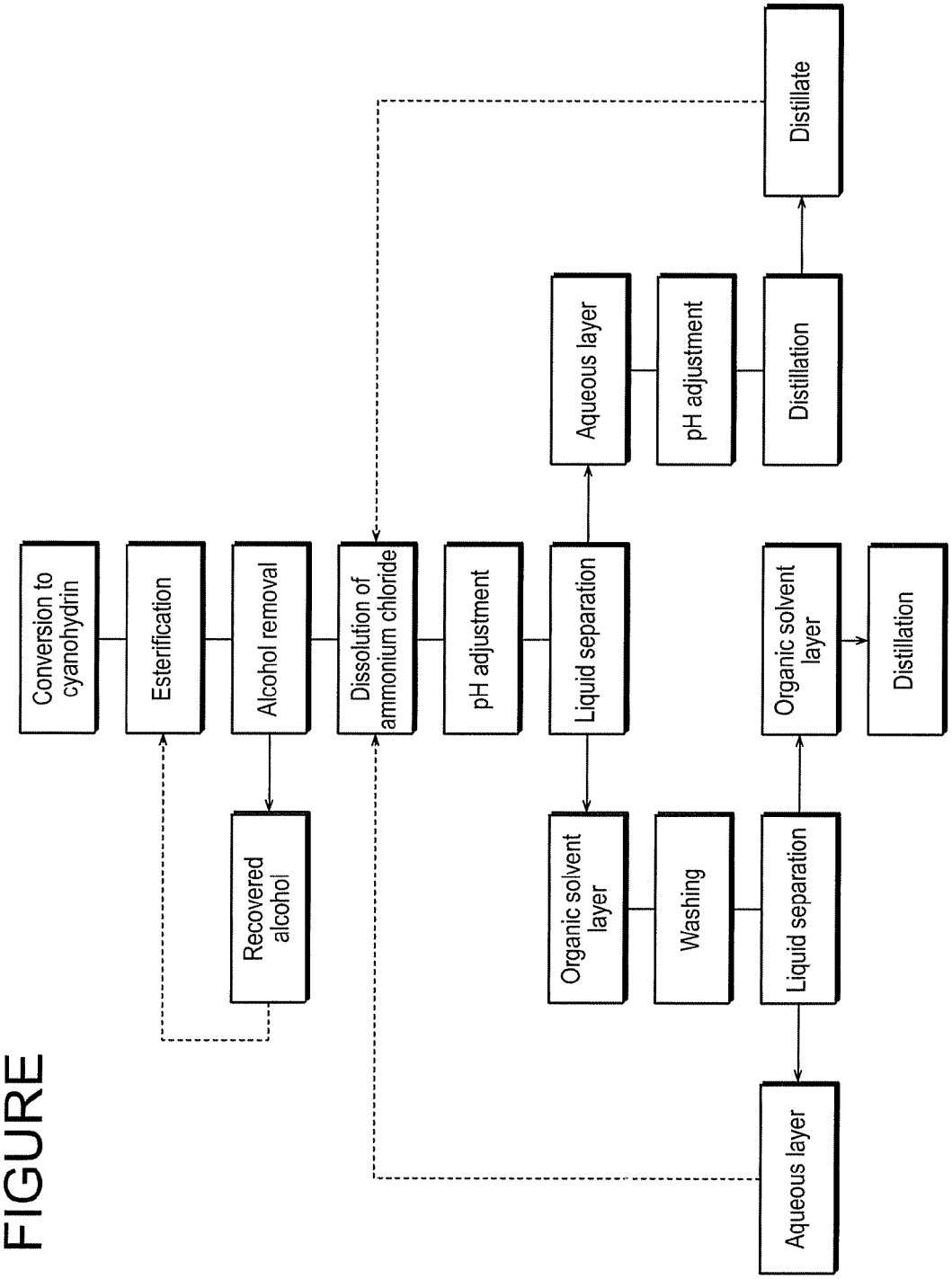
FIGURE

METHOD FOR PRODUCING 2-HYDROXYESTER COMPOUND

TECHNICAL FIELD

The present invention relates to a method for producing a 2-hydroxyester compound.

BACKGROUND ART

A 2-hydroxyester compound is an industrially important compound as intermediates of raw materials of medicine and pesticide or raw materials of photographic chemicals. As a method for producing a 2-hydroxyester compound, there is a method for using an amide, an alcohol and a formate ester as starting raw materials; a method for using a 2-hydroxycarboxylic acid and an alcohol; and also a method for using a cyanohydrin compound and an alcohol; or the like. Among these, because a cyanohydrin compound can be easily prepared from an aldehyde and hydrocyanic acid, various methods for producing a 2-hydroxyester compound by using a cyanohydrin compound as a starting raw material have been proposed.

For example, there is a method for producing 2-hydroxyfatty acid esters by a reaction of ketone cyanohydrin and sulfuric acid, followed by estrification of the reaction product and an alcohol, and by the addition thereto of an anhydrous sulfate salt of an alkali metal or the like (U.S. Pat. No. 2,041,820).

In addition, there is also a method for producing a 2-hydroxyester compound in high yield, by subjecting a cyanohydrin compound to a reaction with an acid such as hydrogen chloride or the like, in an alcohol solvent in a first step to synthesize a hydrochloric acid salt of an imino ether, followed by subjecting to hydrolysis by the addition of water, after removing an unreacted acid in a second step (JP-A-4-230241). In a conventional method according to a reaction among 2-hydroxynitriles, an alcohol and hydrogen chloride gas, reaction time is long such as from 12 to 15 hours, and continuous contact of the reaction mixture solution with HCl flow is required during the reaction, which makes operation troublesome and also provides low yield of an ester.

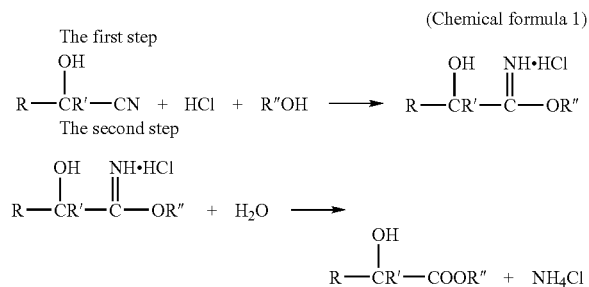

(Chemical formula 1)

In addition, there is also a method for subjecting a specific cyanohydrin compound to a reaction with water and phosphoric acid, followed by esterification by the addition of an alcohol to the reaction product (JP-A-6-247895). The method is proposed in view of problems that co-occurrence of an etherification reaction of a hydroxycarboxylate ester, which is a reaction product, and an alcohol cannot be avoided, which results in contamination of an alkoxycarboxylate ester, as a byproduct, in a reaction product, when a strong acid such as sulfuric acid or hydrochloric acid is used as an acid, and the method features in using phosphoric acid. A reaction by using phosphoric acid proceeds in high selectivity, because side reactions, which generate etherified substances, are suppressed. As shown in the following formulae, the reaction aims at amidation by action of water and phosphoric acid to a cyanohydrin compound, followed by esterification by an alcohol.

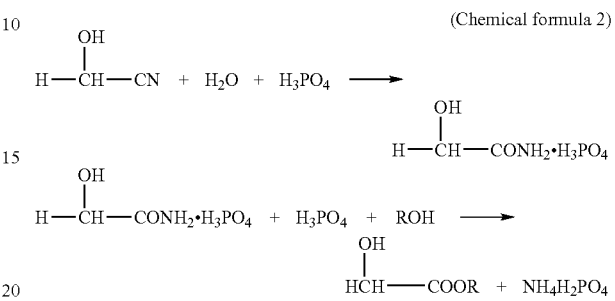

(Chemical formula 2)

In addition, there is also a method for esterification by subjecting specific amount of water and specific amount of sulfuric acid to a reaction with a specific cyanohydrin compound, followed by the addition of an alcohol to the reaction product (JP-A-6-247896). The method aims at proceeding the reaction in high selectivity by suppressing side reactions generating etherified compounds, by amidation by action of water and sulfuric acid to a cyanohydrin compound, followed by esterification with an alcohol, and while continuously supplying water-containing an alcohol to this reaction mixture, by distillating a hydroxycarboxylate ester generating at the same time.

It should be noted that, in the case where a cyanohydrin compound is used as a raw material, because a nitrogen atom composing a cyano group is reduced and finally converted to ammonia and discharged, ammonium sulfate, ammonium nitrate, ammonium phosphate, ammonium chloride or the like is by-produced corresponding to kind of an acid to be used. As a method for fractionating such an ammonium salt, for example, there is a method for recovering a 2-hydroxyester compound by distillation, by the addition of sodium sulfate to a slurry of a reaction solution containing an ammonium salt, an alcohol, a 2-hydroxyester compound and the like (U.S. Pat. No. 2,041,820), or a method for subjecting a slurry of a reaction solution to solid-liquid separation (JP-A-4-230241).

DISCLOSURE OF THE INVENTION

Problem to be Solved by the Invention

However, a method described in U.S. Pat. No. 2,041,820 may lower yield in some cases caused by easy generation of side reactions because a reaction is carried out in an anhydrous state. In addition, in the case where a cyanohydrin compound is used as a raw material, because a nitrogen atom composing a cyano group is reduced and finally converted to ammonium and discharged, an insoluble ammonium sulfate is generated when sulfuric acid is used as an acid, which requires treatment load. It should be noted that, in view of treatment load of ammonium sulfate, situation is the same also in a method described in JP-A-6-247896. In addition, in a method described in JP-A-4-230241, where a mixture of a cyanohydrin compound and an alcohol is used, in the case where amount of hydrogen chloride to be added to the mixture is small, stirring becomes difficult due to reduced fluidity of a slurry-like reaction product, therefore a large quantity of a reaction solvent is required in advance. However, in the case where amount of hydrogen chloride is equal to or higher than two moles, removal operation of the excessively added acid is also required. It should be noted that, as for a method described in JP-A-6-247895, where amidation is carried out by using phosphoric acid, treatment of phosphoric acid-based waste water discharged may be difficult, depending on plant site location, according to Water Pollution Prevention Law.

In addition, in any of the methods in the above-described U.S. Pat. No. 2,041,820, JP-A-4-230241, JP-A-6-247895 and JP-A-6-247896, the reaction is carried out in two-stages, where the second step is carried out after obtaining a reaction product in the first step, which makes practical reaction operation troublesome. It should be noted that a cyanohydrin compound, as described above, provides different reactions depending on addition order of substances, therefore also provides different intermediates to be formed. For example, a cyanohydrin compound forms a hydrochloric acid salt of an amide by water in the presence of hydrochloric acid, and then forms an ester substance by subjecting to a reaction with an alcohol. On the other hand, a reaction of an alcohol to a cyanohydrin compound in the presence of hydrochloric acid first forms a hydrochloric acid salt of an imino ether, and forms a corresponding ester substance by hydrolysis when water is added thereto.

It should be noted that a cyanohydrin compound can be easily prepared in a reaction solution by action of hydrocyanic acid to a carbonyl group of an aldehyde or a ketone. Therefore, when a corresponding 2-hydroxyester compound can be produced from the reaction solution without isolating a cyanohydrin compound, a separation step from an unreacted hydrocyanic acid becomes unnecessary. In addition, when the residual hydrocyanic acid can be treated at the same time in a treatment step of other undesired substances, treatment load of the residual hydrocyanic acid is reduced. For example, in taking methyl 2-hydroxybutanoate (hereafter abbreviated as MHBA) as a 2-hydroxyester compound, because MHBA has dissolving capability of an ammonium salt such as ammonium chloride or the like, a filtrate after solid-liquid separation contains substantial amount of ammonium chloride. Heating of the filtrate to purify MHBA by distillation generates thermal decomposition of MHBA due to presence of ammonium chloride, which lowers yield. In addition, trying to flow out MHBA contained in ammonium chloride after the solid-liquid separation, to enhance yield, requires a large quantity of a solvent. In addition, in producing a 2-hydroxyester compound, it is known that there are such cases that an alkoxyl group is generated by a reaction of a hydroxyl group present in a molecule with an alcohol; a dimer is generated by a reaction between a hydroxyl group and a carbonyl group; or 2-hydroxycarboxylic acid is generated by a reaction of a 2-hydroxyester compound with one molecule of water.

In view of the above circumstances, the present invention provides a method for producing a 2-hydroxyester compound, which enables an easy-to-use synthesis reaction and waste solution treatment, by using a cyanohydrin compound as a raw material.

Means for Solving the Problems

The present inventors have studied in detail a synthesis reaction of a 2-hydroxyester compound by using a cyanohydrin compound as a raw material, and found that, although an objective 2-hydroxyester compound has been produced conventionally by executing a first stage for reacting water or an alcohol to a cyanohydrin compound in the presence of an acid, and from the resulting intermediate in a subsequent second stage, a 2-hydroxyester compound can be produced from a cyanohydrin compound in a single stage, by introducing an acid to a mixture of a cyanohydrin compound, an alcohol, an organic solvent and water, without isolating intermediates such as an amide substance or a hydrochloric acid salt of an imino ether or the like, and also with reduced generation of by-products such as an alkoxyl substance, or a 2-hydroxyester dimer, or 2-hydroxycarboxylic acid and the like.

Namely, the present invention provides a method for producing a 2-hydroxyester compound represented by the general formula (1) (provided that ethyl 2-hydroxy-4-phenylbutyrate is excluded), which comprises a first step in which an acid is introduced into a mixture of a cyanohydrin compound represented by the general formula (2), an alcohol, an organic solvent and water:

(Chemical Formula 3)

$$R^1\text{—CH(OH)—COOR}^2 \quad (1)$$

$$R^1\text{—CH(OH)(CN)} \quad (2)$$

Wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

Further, the present invention provides a method for producing a 2-hydroxyester compound represented by the above general formula (1) (provided that ethyl 2-hydroxy-4-phenyl-butyrate is excluded) which comprises the first step for introducing an acid into a mixture of a cyanohydrin compound represented by the general formula (2), an alcohol, an organic solvent and water; the second step for removing an alcohol from a reaction solution obtained in the first step; the third step for separating a residual reaction solution obtained in the second step to an organic solvent layer and an aqueous layer by the addition of water to the residual reaction solution; and the fourth step for recovering a 2-hydroxyester compound from the organic solvent layer obtained in the third step.

EFFECTS OF THE INVENTION

According to the present invention, a 2-hydroxyester compound can be produced from a cyanohydrin compound in high yield, by a single-stage reaction, and treatment to isolate an intermediate is also not necessary. In particular, in the case where a reaction solution of hydrocyanic acid and an aldehyde is used as a cyanohydrin compound, waste solution treatment can be carried out extremely efficiently, as compared with separate treatment of waste solutions discharged from a production process of a cyanohydrin compound, and a production process of a 2-hydroxyester compound.

BRIEF DESCRIPTION OF THE DRAWING

FIG. 1 is a schematic drawing of a method for producing a 2-hydroxyester compound of the present invention.

BEST MODE FOR CARRYING OUT THE INVENTION

Outline of a method for producing a 2-hydroxyester compound of the present invention is shown in FIG. 1. Explanation will be given below with reference to FIG. 1, on a method for producing a 2-hydroxyester compound of the present invention, in the order of the steps, by taking production of methyl 2-hydroxybutanoate (MHBA) as an example. However, the present invention should not be limited to embodiment only to be described below.

(1) A Reaction Step

The first aspect of the present invention is a method for producing a 2-hydroxyester compound represented by the general formula (1) (provided that ethyl 2-hydroxy-4-phenyl-butyrate is excluded), wherein an acid is introduced into a mixture of a cyanohydrin compound represented by the general formula (2), an alcohol, an organic solvent and water.

(Chemical Formula 4)

Wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

As an aliphatic hydrocarbon group having 1 to 12 carbon atoms, which composes $R^1$, a linear alkyl group such as a methyl group, an ethyl group, a propyl group, an isopropyl group, a butyl group, a pentyl group, an octyl group, a tetradecyl group, an octadecyl group or the like; and a branched alkyl group such as an isopropyl group, a sec-butyl group, a tert-butyl group, a 2-methyloctyl group or the like is included. As an alicyclic hydrocarbon group having 3 to 12 carbon atoms, a cyclopropyl group, a cyclobutyl group, a cyclopentyl group, a cyclohexyl group, a cycloheptyl group, a cyclooctyl group or the like is included. As a substituent, a halogen group, a nitro group or the like is included. In addition, as a substituted or unsubstituted aryl group having 3 to 14 carbon atoms, a phenyl group, an o-, m-, or p-tolyl group, a 2,3-, or 2,4-xylyl group, a cumenyl group, a mesityl group, a naphthyl group, an anthryl group, a phenanthryl group, a biphenylyl group, and a pyrenyl group or the like is included; and as an arylalkyl group, a benzyl group, a phenethyl group, a benzhydryl group, a trityl group or the like is included. As a substituent, an alkyl group, an alkoxy group, a halogen group, a nitro group or the like is included. In the present invention, it is preferable that $R^1$ is a hydrogen atom, a methyl group, an ethyl group, a propyl group, a butyl group, or a 3-methoxyphenyl group.

As an alkyl group having 1 to 12 carbon atoms, which composes $R^2$, an alkyl group described in the above $R^1$ is similarly used preferably. In addition, it is preferable that $R^2$ is a methyl group, an ethyl group, a propyl group or an isopropyl group.

It should be noted that, in a cyanohydrin compound represented by the above formula (2), which is used as a raw material in a production method of the present invention, $R^1$ is also the same as $R^1$ in the above formula (1). In addition, an alcohol is that represented by $R^2OH$, and $R^2$ is also the same as $R^2$ in the above formula (1).

Characteristics of the present invention resides in producing a 2-hydroxyester compound in one stage, by using a mixture of the above cyanohydrin compound added with the above an alcohol, an organic solvent and water, and introducing an acid thereto, without taking out an intermediate and also, without interruption of a reaction. In addition, a method for charging the above an alcohol, an organic solvent and hydrogen chloride or an acid into the above cyanohydrin compound and water is not especially limited, and a plurality of these substances may be charged simultaneously. A reaction step will be shown below.

(Chemical formula 5)

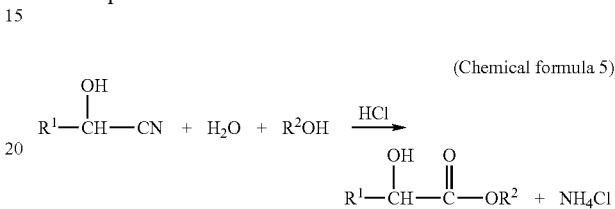

In the present invention, after a charging operation of a cyanohydrin compound, an alcohol, an organic solvent and water, and an operation of the addition of an acid, only a heating operation is left. Therefore, operations for solid-liquid separation, distillation, concentration and the like to separate an intermediate are not necessary, and interruption of the reaction to newly add a raw material is not necessary. In addition, because the reaction can be carried out under normal pressure, a pressurized reaction apparatus such as an autoclave or the like is not required, which provides excellent safety and operationality. Further, it also provides high yield of esterification. In addition, by the addition of water in the presence of an organic solvent, which is inert to the reaction and has a solubility thereof to water of equal to or lower than 8% by mass, to dissolve an ammonium salt, the ammonium salt can be recovered in an aqueous layer after two-layer separation, in the separation step afterwards, and the ammonium salt and a 2-hydroxyester compound contained in the reaction solution can be separated efficiently, therefore concentration of the ammonium salt contained in the organic solvent layer can be lowered.

As for an acid to be used in the present invention, an inorganic acid such as hydrochloric acid, sulfuric acid, nitric acid or the like is included. In addition, an organic acid such as para toluene sulfonic acid, formic acid, acetic acid or the like is included. In particular, it is preferable that hydrogen chloride is used.

As the organic solvent to be used in the present invention, an organic solvent, which is inert to a reaction and has a solubility thereof to water of equal to or lower than 8% by mass, is preferable. For example, it is preferable to be one or more selected among an aromatic hydrocarbon having 6 to 12 carbon atoms such as benzene, toluene, xylene, chlorobenzene or the like; an aliphatic hydrocarbon having 6 to 18 carbon atoms or the like; an ether such as diethyl ether, methyl-t-butyl ether or the like; and a chlorinated hydrocarbon such as chloroform, methylene chloride or the like. It is more preferable to be benzene, toluene, xylene, chlorobenzene, a saturated aliphatic hydrocarbon having 6 to 18 carbon atoms and methylene chloride. In particular, it is preferable to use toluene, because dissolution capability of a 2-hydroxyester compound is high, and solubility to water is low, and further recovery thereof is easy and it is inert.

Concentration of a cyanohydrin compound to be added to the organic solvent is preferably, in general, from 5.0 to 60.0% by mass, more preferably from 20.0 to 40.0% by mass, and particularly preferably from 26.0 to 37.0% by mass, although it differs depending on amounts of water to be added and an alcohol. The concentration over 60.0% by mass provides too high solid content formed in imino-etherification, which could make stirring of a slurry difficult. On the other hand, the concentration below 5.0% by mass could make the solvent recover step troublesome.

The alcohol to be added are theoretically 1 mole relative to 1 mole of a cyanohydrin compound, however, in consideration of reaction yield, it is preferably from 1 to 5 moles, more preferably from 1.5 to 4 moles, and particularly preferably from 2 to 4 moles. The amount below 1 mole lowers yield, while the amount over 5 moles could make removal operation of the excessively added an alcohol troublesome.

In addition, the addition amount of water, particularly in the case where hydrogen chloride is blown as an acid, is theoretically 1 mole relative to 1 mole of the cyanohydrin compound, however, in consideration of reaction yield, it is preferably from 0.8 to 2 moles, more preferably from 0.9 to 1.5 moles, and particularly preferably from 0.9 to 1.2 moles. The amount below 0.8 mole lowers yield, while the amount over 2 moles could also lower yield. However, an acid, which can form a salt with an atom contained in $R^1$ or $R^2$, is not included in introduction amount of the above acid. Here, as an atom contained in $R^1$ or $R^2$, for example, a nitrogen atom of an amine contained in $R^1$ or $R^2$ is included. In particular, by the addition of water in the above range before blowing hydrogen chloride, fluidity of slurry of a reaction solution in imino etherification is improved, stirring becomes easy, and further, by suitable amount of water contained in the reaction solution, generation of an alcoxyl compound or a 2-hydroxyester dimer, derived from a hydroxyl group in a molecule of a 2-hydroxyester compound, can be suppressed, and further reactivity and operationality are enhanced. It should be noted that concentration of the above cyanohydrin compound in a mixture solution can be adjusted by suitably selecting amount of the organic solvent, as well as water to be added and an alcohol. By the addition of water in required amount, solubility of a solid substance, which generates during a reaction, to a reaction solution part is enhanced, and further by the addition of the organic solvent, a slurry state of the reaction solution is improved, which enables an easy-to-use and uniform stirring operation. In addition, an operation of the addition of water afterwards for hydrolysis can be avoided.

In the present invention, by using, in particular, hydrogen chloride as an acid, load of waste water treatment can be reduced as compared with the case of using sulfuric acid, which has been used frequently in a conventional method. Namely, in the case where a 2-hydroxyester compound is produced by using a cyanohydrin compound as a raw material, ammonia is by-produced from nitrogen derived from cyanohydrin, which then reacts with sulfuric acid to form ammonium bisulfate, however, because this compound reduces reaction activity, it is necessary to add sulfuric acid in an amount of equal to or more than 1 mole, relative to 1 mole of a cyanohydrin compound. In addition, amount of an alkali necessary to neutralize sulfuric acid contained in a waste solution becomes two times as compared with the case where hydrogen chloride in the same mole amount is neutralized. Therefore, use of hydrochloric acid can reduce treatment amount of the waste water.

An amount of an acid to be used is preferably from 1.0 to 1.5 moles, and more preferably from 1.05 to 1.25 moles, relative to 1 mole of a cyanohydrin compound. The amount below 1 mole reduces reaction acceleration effect, while the amount over 1.5 moles could reduce yield. It should be noted that hydrogen chloride may be supplied in a gas state, or in a liquid state such as an aqueous solution of hydrochloric acid or the like, or hydrogen chloride gas and an aqueous solution of hydrochloric acid may be used in combination. Concentration of hydrochloric acid, in the case where an aqueous solution of hydrochloric acid is used, is suitably from 35.0 to 38.0% by mass, and water contained should be included in water concentration of the above mixture solution. However, an acid, which can form a salt with an atom contained in $R^1$ or $R^2$, is not included in introduction amount of the above acid. Here, as an atom contained in $R^1$ or $R^2$, for example, a nitrogen atom and the like of an amine contained in $R^1$ or $R^2$ is included.

Solution temperature in introducing an acid is preferably from 0 to 80° C., more preferably from 25 to 60° C., and particularly preferably from 35 to 45° C. The temperature below 0° C. could lengthen reaction time. On the other hand, the temperature over 80° C. could by-produce water and a chloroalkyl compound by a reaction between an alcohol, which are raw materials, and hydrogen chloride. Also, in the case where an aqueous solution of hydrochloric acid is used as hydrogen chloride, it is preferable that the temperature is adjusted in the above temperature range. Introduction time of hydrogen chloride can be arbitrarily selected depending on productivity and removal efficiency of reaction heat, however, it is from 1 to 20 hours, and particularly from 1 to 15 hours.

In the present invention, after the addition of an acid, an objected 2-hydroxyester compound can be obtained by subjecting a reaction solution to a reaction at a temperature range from 0° C. to reflux temperature under normal pressure, within 20 hours, however, it is more preferable that a first aging and a second aging are carried out at different temperature.

For example, after the addition of an acid, a reaction solution is subjected to aging at a temperature range from 0° C. to reflux temperature under normal pressure, preferably from 35 to 45° C., over 0 hour, and for equal to or shorter than 4 hours, more preferably from 1 to 2 hours. This step is called a first aging. Then, a reaction solution is subjected to aging at a temperature range from 20° C. to reflux temperature under normal pressure, preferably at reflux temperature under normal pressure, over 0 hour, and for equal to or shorter than 15 hours, more preferably from 4 to 12 hours. This step is called a second aging. By changing the temperature in this way, side-reactions can be suppressed in the first aging, and also consumption amount of an acid and an alcohol can be suppressed by subjecting most part of the charged acid to a reaction, and alkoxylation of a hydroxyl group or generation of a dimer can be suppressed, and yield can be enhanced, and also by raising reaction temperature in the second aging, reaction time can be shortened and yield can be improved. It should be noted that, in the present invention, slurry is formed with formation of an objective substance, therefore, it is preferable that a reaction solution is stirred over the first aging and the second aging. In the present invention, because the reaction solution contains an organic solvent, water and an alcohol, and amount of the solution is much, therefore, stirring is also easy.

A cyanohydrin compound to be used in the present invention is not especially limited, as for a production method thereof, as long it is as described above, however, a preferred case is a reaction product of an aldehyde with HCN, represented by the following formula (3). It should be noted that, in the following formula (3), $R^1$ is similar to that described in the above 2-hydroxyester compound.

(Chemical Formula 6)

$$R^1\text{—CHO} + HCN \rightarrow R^1\text{—CH(OH)(CN)} \quad (3)$$

Wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom.

A cyanohydrin compound can be produced by the addition of hydrocyanic acid to a carbonyl group of an aldehyde or a ketone, and a reaction solution contains an objective cyanohydrin compound in a concentration of from 5.0 to 60.0% by mass. In the present invention, this reaction solution can be used as it is, as a cyanohydrin compound. Hydrocyanic acid, if present as an unreacted state, is converted to an alkyl formate and ammonium chloride, in the production process of a 2-hydroxyester compound of the present invention, as shown below.

(Chemical Formula 7)

$$HCN + H_2O + R^2OH + HCl \rightarrow HCOOR^2 + NH_4Cl$$

Wherein, $R^2$ is an alkyl group having 1 to 12 carbon atoms, which may contain an oxygen atom, a sulfur atom or a nitrogen atom.

On the other hand, hydrocyanic acid, which remains in trace amount, can be removed from waste water, in treatment of by-produced sodium chloride. Specifically, in the case of treating waste water containing trace amount of hydrocyanic acid, sodium hydroxide as a strong alkali substance is charged in equal to or higher than equivalent amount relative to an acid, to execute neutralization and to attain a pH of equal to or higher than 13. Ammonia contained is removed by distillation or the like. Then, chlorine or sodium hypochlorite is added to this alkali solution. Hydrocyanic acid is converted to NaCN by alkali treatment, and decomposed to nitrogen and carbon dioxide by oxidative force of sodium hypochlorite. A method for decomposing hydrocyanic acid using alkali treatment by the addition of chlorine or sodium hypochlorite to the alkali solution is called an alkali chlorine method. Reason for removing ammonia in advance of the alkali chlorine method is because sodium hypochlorite is consumed uselessly when ammonia contained is oxidized. A reaction formula of the alkali chlorine method is shown below.

(Chemical Formula 8)

$$2NaCN + 5NaOCl + H_2O \rightarrow N_2 + 3NaCl + 2NaHCO_3$$

For example, the case where hydrogen chloride is used instead of sulfuric acid, in the present invention, is particularly excellent in the case of containing such unreacted hydrocyanic acid. Namely in the case of executing alkali treatment as above, sodium hydroxide or the like is used to neutralize an acid contained, and further to make an alkali solution. In this case, use amount of sodium hydroxide to neutralize sulfuric acid is required two times as compared with the case of neutralizing hydrochloric acid. In the case of treating waste water, a sodium salt generating by neutralization is required to be dissolved to avoid clogging of a pipeline or the like and to prevent deposition of crystal, however, solubility of sodium sulfate and solubility of sodium chloride to water at 10° C. are 8.26% by mass and 26.31% by mass, respectively; in this way, sodium chloride has 3.2 times solubility of sodium sulfate. Because molecular weight of sodium sulfate is 2.4 times of sodium chloride, in comparing amount of waste water in the case of using sulfuric acid, and amount of waste water in the case of using hydrochloric acid, the former is 8.3 times of the latter. Therefore, in particular, in the case where a cyanohydrin compound is prepared by using hydrocyanic acid as a raw material, and trace amount of hydrocyanic acid remains in a reaction solution of a cyanohydrin compound, the residual hydrocyanic acid can be fractionated at the same time as treatment of a waste solution containing ammonium chloride, which is discharged from a reaction system of a 2-hydroxyester compound, and amount of the waste solution to be treated can be reduced, in particular, by using hydrogen chloride in the production process of a 2-hydroxyester compound.

(2) An Alcohol Removal Step

The first aspect of the present invention is to provide a method for efficiently producing a 2-hydroxyester compound, as the above description (1), however, by the further addition of the following steps (2) to (5) after that, a series of production method comprising purification of a 2-hydroxyester compound, and at the same time reusing a reaction solution at the next producing cycle is provided.

Namely, the second aspect of the present invention is a method for producing a 2-hydroxyester compound represented by the general formula (1) (provided that ethyl 2-hydroxy-4-phenylbutyrate is excluded), which comprises:

the first step for introducing an acid into a mixture of a cyanohydrin compound represented by the general formula (2), an alcohol, an organic solvent and water;

the second step for removing an alcohol from a reaction solution obtained in the first step;

the third step for separating a residual reaction solution obtained in the second step to an organic solvent layer and an aqueous layer by the addition of water to the residual reaction solution; and the fourth step for recovering a 2-hydroxyester compound from the organic solvent layer obtained in the third step:

(Chemical Formula 9)

$$R^1\text{—CH(OH)—COOR}^2 \quad (1)$$

$$R^1\text{—CH(OH)(CN)} \quad (2)$$

Wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

Because the first step is the same as the first aspect of the present invention, explanation here will be omitted. An organic solvent is preferably one that is inert to a reaction and has solubility to water of equal to or lower than 8% by mass. For example, it is preferable to be one or more among an aromatic hydrocarbon having 6 to 12 carbon atoms such as benzene, toluene, xylene, chlorobenzene; an aliphatic hydrocarbon having 6 to 18 carbon atoms; an ether such as diethyl ether, methyl-t-butyl ether; and a chlorinated hydrocarbon such as chloroform, methylene chloride. It is more preferable to be benzene, toluene, xylene, chlorobenzene, a saturated aliphatic hydrocarbon having 6 to 18 carbon atoms and methylene chloride. In particular, it is preferable to use toluene because solubility of a 2-hydroxyester compound is high, and solubility to water is low, and further recovery thereof is easy and it is inert.

In the second step, an alcohol is removed from the reaction solution containing the above-described 2-hydroxyester compound and an ammonium salt. By removal of an alcohol contained in an organic solvent in advance, a 2-hydroxyester compound can be produced in high purity from the organic solvent, in the recovering step of a 2-hydroxyester compound.

Removal of an alcohol may be carried out by distillation under condition enabling to remove an alcohol in distillation of the reaction solution, and in general, a removal temperature is preferably from 60 to 130° C., more preferably from 60 to 100° C., and particularly preferably from 70 to 90° C. The alcohol contained in the reaction solution can be distilled from the reaction solution at the above temperature range. The removal temperature over 130° C. is disadvantageous because a 2-hydroxyester compound contained in the reaction solution may be decomposed by action of water or the ammonium salt present. On the other hand, distillation at the removal temperature below 60° C. requires excess condition of reduced pressure. It should be noted that the pressure may be in a known range as long as being pressure enabling distillation of the above an alcohol.

It should be noted that an alcohol removed in the alcohol removal step may be used as raw materials for producing a 2-hydroxyester compound. In the case where a large quantity of an alkyl formate, having lower boiling point than that of an alcohol, is contained in a recovered alcohol obtained in the alcohol removal step, an alcohol may be fractionally distillated after removal of the alkyl formate.

(3) A Two-Layer Separation Step

In the present step, a reaction solution after alcohol removal is separated to an organic solvent layer and an aqueous layer by the addition of water thereto. Although dissolution of an ammonium salt into the organic solvent cannot be prevented only by solid-liquid separation of an ammonium salt contained in the reaction solution, however, concentration of the ammonium salt contained in the organic solvent can be efficiently reduced, by two-layer separation to the organic solvent layer and the aqueous layer after the addition of water. It should be noted that a 2-hydroxyester compound is mainly dissolved in the organic solvent layer, and an ammonium salt and a cyanohydrin compound are mainly dissolved in the aqueous layer. In the case where the number of carbon atoms of $R^1$ is from 1 to 5, and the number of carbon atoms of $R^2$ is from 1 to 3, in a 2-hydroxyester compound represented by the general formula (1), the 2-hydroxyester compound provides high solubility to water, and a part of, or whole part of the 2-hydroxyester compound dissolves in the aqueous layer.

Because an ammonium salt contained in the reaction solution is insoluble to an organic solvent, it presents as a slurry state, however, by the addition of water, the ammonium salt can be dissolved in water, and the ammonium salt can be removed from the organic solvent. Therefore, an amount of water to be added is required to be such a level as sufficient to dissolve the ammonium salt contained, and should be such a level as enables two-layer separation from the organic solvent. The amount is preferably from 2.6 to 5.0 times by mass, more preferably from 2.6 to 3.0 times by mass, and particularly preferably from 2.6 to 2.8 times by mass of ammonium chloride. There may be a case where a 2-hydroxyester compound dissolves also in water, and the amount of water to be added over 5.0 times by mass may reduce recovery rate of a 2-hydroxyester compound in certain cases. On the other hand, the addition amount of water below 2.6 times by mass dissolves the ammonium salt only incompletely, thus providing an obstacle in liquid separation operation.

Because the reaction solution after alcohol removal, just after distillation, shows the same high temperature as temperature at distillation, water is added preferably after the temperature becomes equal to or lower than 70° C., more preferably equal to or lower than 40° C. In the case where water is added in a state of the temperature being over 70° C., a 2-hydroxyester compound may be subjected to hydrolysis by water due to action of temperature. It should be noted that a temperature of water to be added is not especially limited, however, it is preferably from 0 to 40° C., and more preferably from 20 to 40° C. In the case where the temperature of water to be added is over 40° C., a 2-hydroxyester compound may be decomposed by water in certain cases, although it depends on pH of the reaction solution. On the other hand, the temperature below 0° C. may reduce solubility of the ammonium salt in certain cases.

In addition, after the addition of water, a solution inside a chamber may be subjected to neutralization. It is preferable that a pH of the solution inside the chamber is from 3 to 9, more preferably from 5 to 8, and particularly preferably from 6.5 to 7.5. In the case where the pH is over 9, hydrolysis may be generated even at room temperature. In the case where the pH is below 3, decomposition may be fast in heating at the fourth step for recovering a 2-hydroxyester compound from the organic solvent layer. It should be noted that pH in the present invention should be one at a temperature of 25° C.

(4) A Recovery Step of a 2-hydroxyester Compound from an Organic Solvent Layer

In the present invention, a 2-hydroxyester compound is produced by distillation of the organic solvent layer after two-layer separation obtained in the above step. Because the organic solvent layer has extremely reduced content of water or an ammonium salt, by the above step, there is no risk of hydrolysis by these, even when the organic solvent layer is heated at distillation temperature of a 2-hydroxyester compound, and thus a 2-hydroxyester compound can be produced in high yield.

(5) A Recovery Step of a 2-hydroxyester Compound from an Aqueous Layer

An ammonium salt is contained in the aqueous layer separated in the above two-layer separation step, however, a 2-hydroxyester compound may also be included in certain cases. In the present step, recovery of water and a 2-hydroxyester compound by distillation is carried out after confirming that pH of the aqueous layer is from 3 to 8, and/or adjusting the pH at 3 to 8.

In the case where a 2-hydroxyester compound is contained in this aqueous layer, yield is reduced when the aqueous layer is discharged as it is. On the other hand, recovery thereof by distillation brings about easy hydrolysis of a 2-hydroxyester compound by heating, and reduces recovery efficiency. In particular, in the production process of a 2-hydroxyester compound, an acid is added to a reaction system for hydrolysis in many cases, by which the resulting aqueous layer may show strongly acidic property in certain cases, and hydrolysis is easily generated by heating the aqueous layer. However, it was found out that adjustment of a pH of the aqueous layer at 3 to 8 enables to avoid decomposition of a 2-hydroxyester compound even under heating condition. It is more preferable that the pH of the aqueous layer is adjusted at 4.0 to 7.0, and particularly preferably at 5.0 to 6.0. It should be noted that timing of adjustment of the pH of the aqueous layer is not especially limited, as long as it is carried out before distillation, and for example, the pH may be adjusted at 3 to 8 in the above two-layer separation step by the addition of sodium hydroxide or the like to the reaction solution before alcohol removal, or, at the time of the addition of water to the reaction solution after alcohol removal, or the pH may be adjusted at 3 to 8 before the addition of water to the reaction solution. In this way, the pH of the aqueous layer after two-layer separation is adjusted at 3 to 8 as a result. For the pH adjustment, sodium hydroxide, potassium hydroxide; or a carbonate of an alkaline metal or an alkaline earth metal; an organic acid salt such as sodium acetate or the like; a phosphate salt or the like may be used. It should be noted that, in the case where solution property of the aqueous layer shows a pH of from 3 to 8 without any adjustment, the aqueous layer may be subjected to distillation as it is.

In the second aspect of the present invention, water and a 2-hydroxyester compound are recovered by distillation from the aqueous layer. A 2-hydroxyester compound may be recovered singly, however, in the case where a 2-hydroxyester compound forms an azeotrope composition with water, both are recovered by azeotropic distillation. Distillation condition in this case is preferably such one that can avoid hydrolysis of a 2-hydroxyester compound, and that water and a 2-hydroxyester compound can make an azeotrope, for example, distillation is carried out at a temperature of from 10° C. to 100° C., more preferably from 20° C. to 90° C., and particularly preferably from 30° C. to 80° C. In addition, distillation is carried out under a pressure range of equal to or lower than normal pressure, preferably from 1.2 kPa to 101.3 kPa, more preferably from 2.3 kPa to 70.1 kPa, and particularly preferably from 4.2 kPa to 47.4 kPa. It should be noted that, in a 2-hydroxyester compound represented by the above formula (1) in the present invention, in the case where $R^1$ and $R^2$ is, in particular, a methyl group or an ethyl group, water solubility of these compounds becomes high, and an azeotropic composition with water is easily formed.

It should be noted that when a distillate is reused as water to be added in the separation step to an organic solvent layer and an aqueous layer, in a subsequent producing process, yield can be enhanced because a 2-hydroxyester compound is also reused in the producing process without being discharged. In the case where a large quantity of an alcohol having lower boiling point than that of the distillate is contained in a distillate obtained in the removal step, an azeotrope of a 2-hydroxyester compound and water may be fractionally distillated after removal of the alcohol.

According to the present invention, a 2-hydroxyester compound represented by the above formula (1) can be separated efficiently and in an easy-to-use way, from an ammonium salt from slurry of a reaction solution containing an ammonium salt, an alcohol, a 2-hydroxyester compound and the like, and an objective substance can be easily produced by obtaining an organic solvent, which mainly dissolves a 2-hydroxyester compound, followed by distillation thereof.

In addition, because distillation of the aqueous layer containing a 2-hydroxyester compound and water brings about an azeotrope of both, reuse thereof in the subsequent producing process of a 2-hydroxyester compound enables to enhance yield.

The production method of the present invention has a wide application range, because it can be applied irrespective of a reaction step of a 2-hydroxyester compound, and an ammonium salt can be easily dissolved into an aqueous layer, in particular, by preparation of a reaction solution containing an organic solvent, and by the addition of water thereto.

EXAMPLES

Explanation will be given below specifically on the present invention with reference to Examples, however, the present invention should not be limited to these Examples.

Reference Example 1

Into a four-necked 300-mL glass flask equipped with a stirrer, a thermometer and a reflux condenser, 120.0 g (2.07 moles) of n-propylaldehyde, and triethylamine were charged, and temperature thereof was adjusted at 15° C. by a thermostatic bath. Under maintaining temperature of the solution inside the flask at 15° C., 56.0 g (2.07 moles) of hydrocyanic acid was dropped over 1 hour. After the dropping, the solution was subjected to aging at 15° C. for 1 hour. In this way, a reaction solution of 2-hydroxybutyronitrile containing 97.7% by mass of 2-hydroxybutyronitrile was obtained.

Reference Example 2

A reaction solution of 2-hydroxyvaleronitrile containing 98.6% by mass of 2-hydroxyvaleronitrile was obtained similarly as in Reference Example 1, except that the same mole of n-butylaldehyde was used instead of n-propylaldehyde.

Reference Example 3

A reaction solution of 2-hydroxyhexyronitrile containing 98.6% by mass of 2-hydroxyhexyronitrile was obtained similarly as in Reference Example 1, except that the same mole of n-pentylaldehyde was used instead of n-propylaldehyde.

Reference Example 4

A reaction solution of m-methoxy mandelonitrile containing 99.12% by mass of m-methoxy mandelonitrile was obtained similarly as in Reference Example 1, except that the same mole of m-anisaldehyde was used instead of n-propylaldehyde.

Reference Example 5

Into a four-necked 500-mL glass flask equipped with a stirrer, a thermometer and a reflux condenser, 290.4 g (5.00 moles) of n-propylaldehyde, and triethylamine were charged, and temperature of the solution inside the flask was adjusted at 15° C. under stirring in a thermostatic bath. Under maintaining temperature of the solution inside the flask at 15° C., 141.0 g (5.22 moles) of hydrocyanic acid was dropped. After the dropping, the solution was subjected to aging at 15° C. for 1 hour. In this way, a reaction solution of 2-hydroxybutyronitrile containing 97.7% by mass of 2-hydroxybutyronitrile was obtained.

Reference Example 6

Into a four-necked 500-mL glass flask equipped with a stirrer, a thermometer and a reflux condenser, 384.3 g (4.00 moles) of furfural, and triethylamine were charged, and temperature of the solution inside the flask was adjusted at 15° C. under stirring in a thermostatic bath. Under maintaining temperature of the solution inside the flask at 15° C., 112.8 g (4.17 moles) of hydrocyanic acid was dropped. After the dropping, the solution was subjected to aging at 15° C. for 1 hour. In this way, a reaction solution of 2-hydroxy-2-furanacetonitrile containing 97.7% by mass of 2-hydroxy-2-furanacetonitrile was obtained.

Example 1

Into a four-necked 1-L glass flask equipped with a stirrer, a thermometer and a reflux condenser, 206.4 g of toluene, 206.9 g (6.46 moles) of methanol, 40.7 g (2.26 moles) of water and 180.4 g of a reaction solution of 2-hydroxybutyronitrile (2.07 moles of 2-hydroxybutyronitrile) obtained in the Reference Example 1 were charged, and temperature of the solution inside the flask was adjusted at 40° C. under stirring in a thermostatic bath. Under maintaining temperature of the solution inside the flask at 40° C., 86.3 g (2.37 moles) of hydrogen chloride was blown therein. After that, the solution was subjected to aging at 40° C. for 1 hour. Then, the solution was subjected to aging at reflux temperature of the solution inside the flask for 5 hours. By analysis of the solution inside the flask with gas chromatography using TCD as a detector, it was found that a reaction product was methyl 2-hydroxybutanoate, production amount thereof was 215.9 g (1.83 moles), and yield thereof was 88.3%.

Example 2

Into a 1-L container connected with a stirring apparatus, a thermocouple type thermometer and a heat exchanger for vapor condensation, along with a container for receiving a distillate, 600 g of an esterification reaction solution containing 29.5% by mass of toluene, 30.7% by mass of methyl 2-hydroxybutanoate, 20.2% by mass of methanol, 16.5% by mass of ammonium chloride and the like was charged. The solution inside the container was heated to remove methanol by simple distillation, until temperature inside the container reached 90° C.

After that, the solution inside the container was cooled to 40° C., and 314 g of water and 4.2 g of sodium hydroxide were added. By this addition, pH of an aqueous layer of the solution inside the container was adjusted at 7.1, and ammonium chloride included therein was dissolved into water.

Subsequently, liquid separation operation was carried out to yield 352 g of an organic layer containing 39.7% by mass of toluene and 38.6% by mass of methyl 2-hydroxybutanoate, and 491 g of an aqueous layer containing 9.5% by mass of methyl 2-hydroxybutanoate.

Into a 1-L container having a stirring apparatus, a thermocouple type thermometer and a heat exchanger for vapor condensation, along with a pipeline connected to a container for receiving a distillate and a vacuum pump, whole amount of the aqueous layer obtained in the above-described two-layer separation step was charged. The aqueous layer thus charged was confirmed to have a pH of 6.5. Then, the pH was adjusted at 5.1 with an aqueous solution of 36% hydrochloric acid. After the pH adjustment, pressure inside the distillation system was reduced to 26.7 kPa, and the solution inside the container was heated to recover water and methyl 2-hydroxybutanoate. By this step, 266 g of a distillate containing 16.5% by mass of methyl 2-hydroxybutanoate was obtained. Recovery rate of methyl 2-hydroxybutanoate by the above-described step was 94.2%, and yield thereof based on a raw material was 20.9%.

Into a 500-mL container having a stirring apparatus, a thermocouple type thermometer and a heat exchanger for vapor condensation, along with a pipeline connected to a container for receiving a distillate and a vacuum pump, whole amount of the organic layer obtained in the above-described two-layer separation step was charged, and pressure inside the distillation system was reduced to 26.7 kPa. The solution inside the container was heated to recover toluene by distillation. Then the solution was once cooled and pressure of the distillation system was reduced to 2.7 kPa. By heating and distillation of the solution inside the container, 107.6 g of methyl 2-hydroxybutanoate was obtained. Yield of methyl 2-hydroxybutanoate by the above-described step was 51.3%. Total yield of methyl 2-hydroxybutanoate obtained by each of the distillations of the separated aqueous layer and organic layer was 72.2%.

Example 3

Into a 10-L container having a stirring apparatus, a thermocouple type thermometer and a heat exchanger for vapor condensation, along with a pipeline connected to a container for receiving a distillate, 6304 g of an esterification reaction solution containing 29.5% by mass of toluene, 30.7% by mass of methyl 2-hydroxybutanoate, 20.2% by mass of methanol, 16.5% by mass of ammonium chloride and the like was charged. The solution inside the container was heated to remove methanol by simple distillation, until temperature inside the container reached 90° C.

After that, the solution inside the container was cooled to 40° C., and 3357 g of water was added to dissolve ammonium chloride included therein into water.

Subsequently, liquid separation operation was carried out to obtain 3214 g of an organic layer containing 57.3% by mass of toluene and 32.5% by mass of methyl 2-hydroxybutanoate, and 5743 g of an aqueous layer containing 9.6% by mass of methyl 2-hydroxybutanoate and the like.

Into a 10-L container having a stirring apparatus, a thermocouple type thermometer and a heat exchanger for vapor condensation, along with a pipeline connected to a container for receiving a distillate and a vacuum pump, whole amount of the aqueous layer obtained in the above-described two-layer separation step was charged. The aqueous layer thus charged was confirmed to have a pH of 6.5. Then, the pH was adjusted at 5.4 with an aqueous solution of 36% hydrochloric acid. After the pH adjustment, pressure inside a distillation system was reduced to 26.7 kPa, and the solution inside the container was heated to recover water and methyl 2-hydroxybutanoate. By this step, 3722 g of a distillate containing 13.6% by mass of methyl 2-hydroxybutanoate was obtained. Recovery rate of methyl 2-hydroxybutanoate by the above-described step was 91.8%, and yield thereof based on a raw material was 27.4%.

Into a 6-L container having a stirring apparatus, a thermocouple type thermometer and a heat exchanger for vapor condensation, along with a pipeline connected to a container for receiving a distillate and a vacuum pump, whole amount of the organic layer obtained in the above-described two-layer separation step was charged. Into this organic layer, 31 g of an aqueous solution of 20% sodium hydroxide was added and pH of the solution inside the container was adjusted at 6.8. Subsequently, liquid separation operation was carried out to take out the aqueous layer from the system. Pressure inside the distillation system was reduced to 26.7 kPa, and the solution inside the container was heated to recover toluene by distillation. After that the solution was once cooled and pressure inside the distillation system was reduced to 2.7 kPa. The solution inside the container was heated to obtain methyl 2-hydroxybutanoate by distillation. Yield of methyl 2-hydroxybutanoate by the above-described step was 46.0%. Total yield of methyl 2-hydroxybutanoate obtained by each of the distillations of the separated aqueous layer and organic layer was 73.4%.

Example 4

Into a 1-L container connected with a stirring apparatus, a thermocouple type thermometer and a heat exchanger for vapor condensation, along with a pipeline connected to a container for receiving a distillate, 514.3 g of an esterification reaction solution containing 29.2% by mass of toluene, 30.0% by mass of methyl 2-hydroxybutanoate, 19.8% by mass of methanol, 16.1% by mass of ammonium chloride and the like was charged. The solution inside the container was heated to remove methanol by simple distillation, until temperature inside the container reached 90° C.

After that, the solution inside the container was cooled to 40° C., and 237 g of water and 3.6 g of sodium hydroxide were added. By this addition, pH of an aqueous layer of the solution inside the container was adjusted at 5.3, and ammonium chloride included therein was dissolved into water.

Subsequently, liquid separation operation was carried out to obtain 180.0 g of an organic layer containing 38.9% by mass of toluene and 55.4% by mass of methyl 2-hydroxybutanoate, and 388.2 g of an aqueous layer containing 13.7% by mass (53.1 g) of methyl 2-hydroxybutanoate.

Into a 300-mL container having a stirring apparatus, a thermocouple type thermometer and a heat exchanger for vapor condensation, along with a pipeline connected to a container for receiving a distillate and a vacuum pump, whole amount of the organic layer obtained in the above-described two-layer separation step was charged, and pressure inside the distillation system was reduced to 26.7 kPa. The solution inside the container was heated to recover toluene by distillation. Then the solution was once cooled and pressure inside the distillation system was reduced to 2.7 kPa. By heating and distillation of the solution inside the container, 83.8 g of methyl 2-hydroxybutanoate was obtained. Yield of methyl 2-hydroxybutanoate by the above-described step was 47.8%.

Into a 500-mL container having a stirring apparatus, a thermocouple type thermometer and a heat exchanger for vapor condensation, along with a pipeline connected to a container for receiving a distillate and a vacuum pump, whole amount of the aqueous layer obtained in the above-described two-layer separation step was charged. The aqueous layer thus charged was confirmed to have a pH of 5.2. Without further pH adjustment, the solution was subjected to the distillation step. Then, the pressure inside a distillation system was reduced to 26.7 kPa. The solution inside the container was heated to recover water and methyl 2-hydroxybutanoate by distillation. By this step, 202.0 g of a distillate containing 24.2% by mass (48.9 g) of methyl 2-hydroxybutanoate was obtained. Recovery rate of methyl 2-hydroxybutanoate by the above-described step was 92.1%, and yield thereof based on a raw material was 27.9%. The residual 7.9% is considered to be thermal decomposition. Total yield of methyl 2-hydroxybutanoate obtained by each of the distillations of the separated aqueous layer and organic layer was 75.7%.

Example 5

Into a 1-L container connected with a stirring apparatus, a thermocouple type thermometer and a heat exchanger for vapor condensation, along with a pipeline connected to a container for receiving a distillate, 515.8 g of an esterification reaction solution containing 29.3% by mass of toluene, 29.5% by mass of methyl 2-hydroxybutanoate, 19.0% by mass of methanol, 16.2% by mass of ammonium chloride and the like was charged. The solution inside the container was heated to remove methanol by simple distillation, until temperature inside the container reached 90° C.

After that, the solution inside the container was cooled to 40° C.

Into the container, 190.5 g of the distilled solution containing methyl 2-hydroxybutanoate and water obtained by distillation of the aqueous layer after the two-layer separation of Example 4, 130 g of water, 74.5 g of toluene and 2.5 g of sodium hydroxide were charged, and ammonium chloride was dissolved into water and also pH of the aqueous layer of the solution inside the container was adjusted at 5.3. Subsequently, liquid separation operation was carried out to yield 306.9 g of an organic layer containing 48.1% by mass of toluene and 44.6% by mass of methyl 2-hydroxybutanoate, and 414.4 g of an aqueous layer containing 15.2% by mass (63.1 g) of methyl 2-hydroxybutanoate. Recovery rate of methyl 2-hydroxybutanoate by the above-described step was 94.6%, and total yield of methyl 2-hydroxybutanoate obtained from the above organic layer by a similar method as in Example 4 was 76.1%.

Example 6

Into a four-necked 1-L glass flask equipped with a stirrer, a thermometer and a reflux condenser, 202.5 g of toluene, 265.5 g (5.76 moles) of ethanol, 36.3 g (2.01 moles) of water and 186.1 g of a reaction solution of 2-hydroxyvaleronitrile (1.85 moles of 2-hydroxyvaleronitrile) obtained in the Reference Example 2 were charged, and temperature of the solution inside the flask was adjusted at 40° C. under stirring in a thermostatic bath. Under maintaining temperature of the solution inside the flask at 40° C., 76.9 g (2.11 moles) of hydrogen chloride was blown therein. After that, the solution was subjected to aging at 40° C. for 1 hour, and further to aging at reflux temperature of the solution inside the flask for 12 hours. Then by analysis of the solution inside the flask with gas chromatography using TCD as a detector, it was found that a reaction product was ethyl 2-hydroxyvalerate, production amount was 234.5 g (1.60 moles), and yield was 86.7%.

Example 7

Into a four-necked 1-L glass flask equipped with a stirrer, a thermometer and a reflux condenser, 180.0 g of toluene, 186.6 g (5.82 moles) of methanol, 33.2 g (1.84 moles) of water and 213.5 g of a reaction solution of 2-hydroxyhexyronitrile (1.86 moles of 2-hydroxyhexyronitrile) obtained in the Reference Example 3 were charged, and temperature of the solution inside the flask was adjusted at 40° C. under stirring in a thermostatic bath. Under maintaining temperature of the solution inside the flask at 40° C., 85.0 g (2.33 moles) of hydrogen chloride was blown therein. After that, the solution was subjected to aging at 40° C. for 1 hour, and further to aging at reflux temperature of the solution inside the flask for 12 hours. Then by analysis of the solution inside the flask with gas chromatography using TCD as a detector, it was found that a reaction product was methyl 2-hydroxyhexanoate, production amount was 236.8 g (1.62 moles), and yield was 87.1%.

Example 8

Into a four-necked 1-L glass flask equipped with a stirrer, a thermometer and a reflux condenser, 228.1 g of toluene, 219.1 g (6.84 moles) of methanol, 39.0 g (2.17 moles) of water and 359.7 g of a reaction solution of m-methoxy mandelonitrile (1.85 moles of m-methoxy mandelonitrile) obtained in the Reference Example 4 were charged, and temperature of the solution inside the flask was adjusted at 40° C. under stirring in a thermostatic bath. Under maintaining temperature of the solution inside the flask at 40° C., 99.7 g (2.72 moles) of hydrogen chloride was blown therein. After that, the solution was subjected to aging at 40° C. for 1 hour, and further to aging at reflux temperature of the solution inside the flask for 9 hours. Then by analysis of the solution inside the flask with gas chromatography using TCD as a detector, it was found that a reaction product was methyl m-methoxy mandelate, production amount was 283.5 g (1.44 moles), and yield was 78.1%.

Example 9

Into a four-necked 1-L glass flask equipped with a stirrer, a thermometer and a reflux condenser, 207.0 g of toluene, 331.6 g (10.35 moles) of methanol, and 174.8 g of a reaction solution of 2-hydroxybutyronitrile (2.01 moles of 2-hydroxybutyronitrile) obtained in the Reference Example 5 were charged, and temperature of the solution inside the flask was adjusted at 40° C. under stirring in a thermostatic bath. Under maintaining temperature of the solution inside the flask at 40° C., 229.5 g of an aqueous solution of 36% hydrochloric acid (2.27 moles of hydrogen chloride) was dropped therein over 2 hours. After the dropping, the solution was subjected to aging at 40° C. for 1 hour, and then, by raising temperature, to aging at reflux temperature for 5 hours. After the aging, the reaction solution was filtered to remove a by-produced crystal. An objective substance contained in the crystal was recovered into the filtrate by washing the crystal with 230 g of toluene. By liquid separation of the filtrate separated into two layers and each analysis thereof with gas chromatography, it was found that a reaction product was methyl 2-hydroxybutanoate, total production amount contained in these two layers was 124.7 g (1.056 moles), and yield was 52.8%.

Example 10

Into a four-necked 1-L glass flask equipped with a stirrer, a thermometer and a reflux condenser, 207.0 g of toluene, 199.0 g (6.21 moles) of methanol, 38.4 g (2.13 moles) of water and 248.6 g of a reaction solution of 2-hydroxy-2-furanacetonitrile (1.98 moles of 2-hydroxy-2-furanacetonitrile) obtained in the Reference Example 6 were charged, and temperature of the solution inside the flask was adjusted at 40° C. under stirring in a thermostatic bath. Under maintaining temperature of the solution inside the flask at 40° C., 82.7 g (2.27 moles) of hydrogen chloride was blown therein. After the blowing, the solution was subjected to aging at 40° C. for 1 hour, and then, by raising temperature, to aging at reflux temperature for 5 hours. After the aging, by analysis of the reaction solution with gas chromatography, it was found that a reaction product was methyl 2-hydroxy-2-furanacetate, production amount was 87.4 g (0.56 moles), and yield was 28.3%.

Example 11

Into a four-necked 1-L glass flask equipped with a stirrer, a thermometer and a reflux condenser, 207.0 g of toluene, 199.0 g (6.21 moles) of methanol, 29.2 g (1.621 moles) of water and 174.8 g of a reaction solution of 2-hydroxybutyronitrile (2.01 moles of 2-hydroxybutyronitrile) obtained in the Reference Example 5 were charged, and temperature of the solution inside the flask was adjusted at 40° C. under stirring in a thermostatic bath. Under maintaining temperature of the solution inside the flask at 40° C., 231.5 g (2.27 moles) of 96% sulfuric acid was dropped therein. After the dropping, the solution was subjected to aging at 40° C. for 1 hour, and then, by raising temperature, to aging at reflux temperature for 5 hours. After the aging, by analysis of the reaction solution with gas chromatography, it was found that a reaction product was methyl 2-hydroxybutanoate, production amount was 162.3 g (1.374 moles), and yield was 68.4%.

Comparative Example 1

Into a four-necked 1-L glass flask equipped with a stirrer, a thermometer and a reflux condenser, 370.9 g (11.58 moles) of anhydrous methanol, and 180.4 g of a reaction solution of 2-hydroxybutyronitrile (2.07 moles of 2-hydroxybutyronitrile) were charged, and temperature of the solution inside the flask was adjusted at 0° C. under stirring in a thermostatic bath. Under maintaining temperature of the solution inside the flask at 0° C., 216.3 g (5.93 moles) of hydrogen chloride was blown therein. The resulting mixture was subjected to aging at 0° C. for 2 hours by stirring. During the aging, a hydrochloric acid salt of an imino ether was deposited and provided a concentrated slurry, which made stirring difficult. Therefore, the stirrer was taken out of the flask, the reaction slurry was concentrated under reduced pressure to remove hydrogen chloride. It took 6 hours to concentrate under reduced pressure.

The stirrer was installed again to the flask, and refluxing under heating was carried out for 1.5 hours by charging 520.3 g of methanol, 37.2 g (2.064 moles) of water. After the completion of the reaction, 25.0 g of toluene was added to the slurry of the reaction solution (it was used as an internal standard substance for calculating content of methyl 2-hydroxybutanoate by gas chromatography), and by analysis of the supernatant inside the flask with gas chromatography using TCD as a detector, it was found that production amount of methyl 2-hydroxybutanoate was 215.5 g (1.824 moles), and yield was 88.3%.

Comparative Example 2

Into a four-necked 1-L glass flask equipped with a stirrer, a thermometer and a reflux condenser, 232.6 g (2.28 moles) of 96% by mass sulfuric acid was charged, and a mixture of 180.4 g of a reaction solution of 2-hydroxybutyronitrile (2.07 moles of 2-hydroxybutyronitrile) and 41.0 g (2.28 moles) of water was dropped thereto in 50 minutes in ice-water bath. This mixture was heated at 60° C. for 1 hour, and further at 70° C. for 3 hours to be subjected to a hydration reaction. After the hydration reaction, a viscous mixture was obtained by cooling to 20° C. Into this mixture, 199.0 g (6.211 moles) of methanol was added to carry out reflux for 6 hours. After the refluxing, the solution was cooled, however, the reaction mixture was solidified at 18° C., which made stirring impossible. By taking out a part of the reaction mixture, a methanol solution of 20% ammonia was added therein. Then as a result of analysis thereof with gas chromatography using TCD as a detector, generation of methyl 2-hydroxybutanoate was confirmed.

INDUSTRIAL APPLICABILITY

The present invention is useful because a 2-hydroxyester compound, which is useful as intermediates of medicine and pesticide, or photographic chemicals and the like, can be produced in an easy-to-use way.

The present invention is based on Japanese Patent Application No. 2005-229970, filed on Aug. 8, 2005, whose content is incorporated by reference in its entirety.

The invention claimed is:

1. A method for producing a 2-hydroxyester compound represented by the general formula (1) (provided that ethyl 2-hydroxy-4-phenylbutyrate is excluded), comprising introducing an acid into a mixture of a cyanohydrin compound represented by the general formula (2), an alcohol, an organic solvent and water to carry out a reaction in a single stage and without isolating an intermediate:

(Chemical formula 1)

$$R^1—CH(OH)—COOR^2 \quad (1)$$

$$R^1—CH(OH)(CN) \quad (2)$$

wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

2. The method for producing a 2-hydroxyester compound according to claim 1, wherein the addition amount of the alcohol is from 1 to 5 moles relative to 1 mole of the cyanohydrin compound.

3. The method for producing a 2-hydroxyester compound according to claim 1, wherein the organic solvent is inert to a reaction and solubility to water is equal to or lower than 8% by mass.

4. The method for producing a 2-hydroxyester compound according to claim 1, wherein the organic solvent is one or more selected from the group consisting of an aromatic hydrocarbon having 6 to 12 carbon atoms, an aliphatic hydrocarbon having 6 to 18 carbon atoms, an ether, and a chlorinated hydrocarbon.

5. The method for producing a 2-hydroxyester compound according to claim 1, wherein the addition amount of the water is from 0.8 to 2 moles relative to 1 mole of the cyanohydrin compound.

6. The method for producing a 2-hydroxyester compound according to claim 1, wherein the introduction amount of the acid is from 1.0 to 1.5 moles relative to 1 mole of the cyanohydrin compound.

7. The method for producing a 2-hydroxyester compound according to claim 1, wherein introduction of the acid is carried out at a temperature of from 0 to 80° C.

8. The method for producing a 2-hydroxyester compound according to claim 1, wherein the acid is hydrogen chloride.

9. The method for producing a 2-hydroxyester compound according to claim 1, wherein the cyanohydrin compound represented by the general formula (2) is a reaction product of a reaction represented by the reaction formula (3) in which an aldehyde reacts with HCN:

(Chemical formula 2)

$$R^1—CHO+HCN \rightarrow R^1—CH(OH)(CN) \quad (3)$$

wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom.

10. The method for producing a 2-hydroxyester compound according to claim 1, wherein concentration of a cyanohydrin compound contained in the mixture is from 5.0 to 60.0% by mass.

11. A method for producing a 2-hydroxyester compound represented by the general formula (1) (provided that ethyl 2-hydroxy-4-phenylbutyrate is excluded), which comprises:

the first step for introducing an acid into a mixture of a cyanohydrin compound represented by the general formula (2), an alcohol, an organic solvent and water to carry out a reaction in a single stage and without isolating an intermediate;

the second step for removing an alcohol from a reaction solution obtained in the first step;

the third step for separating a residual reaction solution obtained in the second step to an organic solvent layer and an aqueous layer by the addition of water to the residual reaction solution; and the fourth step for recovering a 2-hydroxyester compound from the organic solvent layer obtained in the third step;

(Chemical formula 3)

$$R^1—CH(OH)—COOR^2 \quad (1)$$

$$R^1—CH(OH)(CN) \quad (2)$$

wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom; and $R^2$ is an alkyl group having 1 to 12 carbon atoms, which may contain an oxygen atom, a sulfur atom or a nitrogen atom.

12. The method for producing a 2-hydroxyester compound according to claim 11, which comprises a step for obtaining a distillate containing a 2-hydroxyester compound and water by distillation of the aqueous layer obtained in the third step.

13. The method for producing a 2-hydroxyester compound according to claim 11, wherein pH of the aqueous layer obtained in the third step is adjusted at from 3 to 8.

14. The method for producing a 2-hydroxyester compound according to claim 12, wherein the distillate is used as a substitution of water to be added in the third step.

15. The method for producing a 2-hydroxyester compound according to claim 11, wherein the addition amount of the alcohol is from 1 to 5 moles relative to 1 mole of the cyanohydrin compound.

16. The method for producing a 2-hydroxyester compound according to claim 11, wherein the organic solvent is inert to a reaction and solubility to water is equal to or lower than 8% by mass.

17. The method for producing a 2-hydroxyester compound according to claim 11, wherein the organic solvent is one or more selected from the group consisting of an aromatic hydrocarbon having 6 to 12 carbon atoms, an aliphatic hydrocarbon having 6 to 18 carbon atoms, an ether, and a chlorinated hydrocarbon.

18. The method for producing a 2-hydroxyester compound according to claim 11, wherein the addition amount of the water is from 0.8 to 2 moles relative to 1 mole of the cyanohydrin compound.

19. The method for producing a 2-hydroxyester compound according to claim 11, wherein the introduction amount of the acid is from 1.0 to 1.5 moles relative to 1 mole of the cyanohydrin compound.

20. The method for producing a 2-hydroxyester compound according to claim 11, wherein introduction of the acid is carried out at a temperature of from 0 to 80° C.

21. The method for producing a 2-hydroxyester compound according to claim 11, wherein the acid is hydrogen chloride.

22. The method for producing a 2-hydroxyester compound according to claim 11, wherein the cyanohydrin compound represented by the general formula (2) is a reaction product of a reaction represented by the reaction formula (3) in which an aldehyde reacts with HCN:

(Chemical formula 4)

$$R^1-CHO + HCN \rightarrow R^1-CH(OH)(CN) \quad (3)$$

wherein, $R^1$ is a hydrogen atom, a substituted or unsubstituted aliphatic hydrocarbon group having 1 to 12 carbon atoms, which may contain an oxygen atom, a sulfur atom or a nitrogen atom, a substituted or unsubstituted alicyclic hydrocarbon group having 3 to 12 carbon atoms, which may contain an oxygen atom, a sulfur atom or a nitrogen atom, and a substituted or unsubstituted aryl group or aralkyl group having 3 to 14 carbon atoms, which may contain an oxygen atom, a sulfur atom or a nitrogen atom.

23. The method for producing a 2-hydroxyester compound according to claim 11, wherein concentration of a cyanohydrin compound contained in the mixture is from 5.0 to 60.0% by mass.

24. The method for producing a 2-hydroxyester compound according to claim 11, wherein the 2-hydroxyester compound is methyl 2-hydroxybutanoate.

* * * * *